US009441029B2

(12) United States Patent
Stefano et al.

(10) Patent No.: US 9,441,029 B2
(45) Date of Patent: Sep. 13, 2016

(54) VEGF ANTAGONIST COMPOSITIONS AND USES THEREOF

(75) Inventors: James Stefano, Hopkinton, MA (US); Clark Pan, Framingham, MA (US); Huawei Qiu, Framingham, MA (US); Michael O'Callaghan, Framingham, MA (US); Gloria Matthews, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 225 days.

(21) Appl. No.: 13/814,182

(22) PCT Filed: Aug. 5, 2011

(86) PCT No.: PCT/US2011/046802
§ 371 (c)(1),
(2), (4) Date: Aug. 14, 2013

(87) PCT Pub. No.: WO2012/019128
PCT Pub. Date: Feb. 9, 2012

(65) Prior Publication Data
US 2013/0324465 A1    Dec. 5, 2013

Related U.S. Application Data

(60) Provisional application No. 61/371,546, filed on Aug. 6, 2010.

(51) Int. Cl.
| *A61K 38/00* | (2006.01) |
| *C07K 14/435* | (2006.01) |
| *C07K 14/71* | (2006.01) |
| *C12N 9/12* | (2006.01) |

(52) U.S. Cl.
CPC ............... *C07K 14/71* (2013.01); *C12N 9/12* (2013.01)

(58) Field of Classification Search
None
See application file for complete search history.

(56) References Cited

U.S. PATENT DOCUMENTS

| | | | |
|---|---|---|---|
| 4,847,325 A * | 7/1989 | Shadle | A61K 47/48176 514/1.3 |
| 5,089,833 A | 2/1992 | Takahashi et al. | |
| 5,116,964 A | 5/1992 | Capon et al. | |
| 5,155,027 A | 10/1992 | Sledziewski et al. | |
| 5,336,603 A | 8/1994 | Capon et al. | |
| 5,567,584 A | 10/1996 | Sledziewski et al. | |
| 5,712,380 A | 1/1998 | Kendall et al. | |
| 5,827,702 A | 10/1998 | Cuthbertson | |
| 5,843,725 A | 12/1998 | Sledziewski et al. | |
| 6,100,071 A | 8/2000 | Davis-Smyth et al. | |
| 6,204,011 B1 | 3/2001 | Kendall et al. | |
| 6,270,993 B1 | 8/2001 | Shibuya et al. | |
| 6,348,333 B1 | 2/2002 | Niwa et al. | |
| 6,375,929 B1 | 4/2002 | Thomas, Jr. et al. | |
| 6,378,526 B1 | 4/2002 | Bowman et al. | |
| 6,383,486 B1 | 5/2002 | Davis-Smyth et al. | |
| 6,397,849 B1 | 6/2002 | Bowman et al. | |
| 6,482,634 B1 | 11/2002 | Wilson et al. | |
| 6,686,200 B1 | 2/2004 | Dong et al. | |
| 6,821,775 B1 | 11/2004 | Kovesdi et al. | |
| 6,897,294 B2 | 5/2005 | Davis-Smyth et al. | |
| 6,943,019 B2 | 9/2005 | Wilson et al. | |
| 6,943,153 B1 | 9/2005 | Manning, Jr. et al. | |
| 7,083,950 B2 | 8/2006 | Stahl et al. | |
| 7,087,411 B2 | 8/2006 | Daly et al. | |
| 7,928,072 B2 | 4/2011 | Scaria et al. | |
| 2002/0098187 A1 | 7/2002 | Ferrara et al. | |
| 2003/0092604 A1 | 5/2003 | Davis-Smyth et al. | |
| 2004/0052785 A1 | 3/2004 | Goodman et al. | |
| 2005/0163798 A1 | 7/2005 | Papadopoulos et al. | |
| 2005/0175624 A1 | 8/2005 | Romero et al. | |
| 2006/0134111 A1 | 6/2006 | Agarwal | |
| 2006/0193830 A1 | 8/2006 | Hauswirth et al. | |
| 2007/0224178 A1 * | 9/2007 | Scaria | C07K 14/475 424/93.21 |

FOREIGN PATENT DOCUMENTS

| | | |
|---|---|---|
| EP | 1183051 A2 | 3/2002 |
| EP | 1238986 A2 | 9/2002 |
| EP | 1621213 | 2/2006 |
| EP | 0928203 | 10/2006 |
| WO | WO9108298 A2 | 6/1991 |
| WO | WO9420146 A1 | 9/1994 |
| WO | WO9421679 A1 | 9/1994 |
| WO | WO9410202 A1 | 11/1994 |
| WO | WO9506743 A2 | 3/1995 |
| WO | WO9613276 A1 | 5/1996 |
| WO | WO 98/13071 | 4/1998 |
| WO | WO9831794 A1 | 7/1998 |

(Continued)

OTHER PUBLICATIONS

Lai, YKY et al., "Potential long-term inhibition of ocular neovascularisation by recombinant adeno-associated virus-mediated secretion gene therapy", Gene Therapy, 9:804-813, 2002.
Mori, K. et al., "AAV-Mediated Gene Transfer of Pigment Epithelium-Derived Factor Inhibits Choroidal Neovascularization", Investigative Opthalmology & Visual Science, 43(6):1994-2000, Jun. 2002.
Campochiaro, Peter A., "Gene therapy for retinal and choroidal diseases", Expert Opin. Biol. Ther., 2(5):537-544, 2002.
Chaum, E. and Hatton, M.P., "Gene Therapy for Genetic and Acquired Retinal Diseases", Survey of Opthalmology, 47(5):449-469, Sep.-Oct. 2002.
Borras, Teresa, "Recent developments in ocular gene therapy", Experimental Eye Research, 76:643-652, 2003.

(Continued)

*Primary Examiner* — Christine J Saoud
*Assistant Examiner* — Jon M Lockard
(74) *Attorney, Agent, or Firm* — Roberta L. Robins; Robins Law Group

(57) ABSTRACT

The invention provides compositions and methods for treating a disease or disorder associated with vascular endothelial growth factor (VEGF). Specifically, the invention relates to an oligomerized VEGF binding domain to provide VEGF antagonism, and thereby treat diseases associated thereof.

32 Claims, 15 Drawing Sheets

(56) References Cited

FOREIGN PATENT DOCUMENTS

| WO | WO 98/51323 | 11/1998 |
|---|---|---|
| WO | WO9855638 A1 | 12/1998 |
| WO | WO9858053 A1 | 12/1998 |
| WO | WO0054813 A2 | 9/2000 |
| WO | WO0075319 A1 | 12/2000 |
| WO | WO0224234 A2 | 3/2002 |
| WO | WO03080648 A2 | 10/2003 |
| WO | WO 2004/085478 | 10/2004 |
| WO | WO2006066086 A1 | 6/2006 |

OTHER PUBLICATIONS

Pleyer, U. and Ritter, T., "Gene therapy in immune-mediated diseases of the eye", Progress in Retinal and Eye Research, 22:277-293, 2003.
Jomary, C. et al., "Adenoassociated Virus Vector-Mediated Gene Transfer to Retinal Cells In Vitro and In Vivo", Investigative Ophthalmology & Visual Science, 36(4):Abstract 3569-556, Mar. 15, 1995.
Ali, R.R. et al., "Gene transfer into the mouse retina mediated by an adeno-associated viral vector", Human Molecular Genetics, 5(5):591-594, 1996.
Hauswirth, W. et al., "Efficient Photoreceptor-Targeted Gene Expression In Vivo Mediated by Recombinant Adeno-Associated Virus", Investigative Ophthalmology & Visual Science, 38(4): Abstract 1193-5:45, Mar. 15, 1997.
Bennett, J. et al., "Real-Time, Noninvasive In Vivo Assessment of Adeno-Associated Virus-Mediated Retinal Transduction", Investigative Ophthalmology & Visual Science, 38:(13):2857-2863, Dec. 1997.
Ali, R.R. et al., "Adeno-Associated Virus Gene Transfer to Mouse Retina", Human Gene Therapy, 9:81-86, Jan. 1, 1998.
Bennett, J. et al., "Stable transgene expression in rod photoreceptors after recombinant adeno-associated virus-mediated gene transfer to monkey retina", Proc. Natl. Acad. Sci., USA, 96:9920-9925, Aug. 1999.
Auricchio, A. et al., "Inhibition of Retinal Neovascularization by Intraocular Viral-Mediated Delivery of Anti-angiogenic Agents", Molecular Therapy, 6(4):490-494, Oct. 2002.
Bok, Dean, "Retinal Transplantation and Gene Therapy", Investigative Ophthalmology & Visual Science, 34(3):473-476, Mar. 1993.
Zack, Donald J., "Ocular Gene Therapy From Fantasy to Forseeable Reality", Arch Ophthalmology, 111:1477-1478, Nov. 1993.
Bennett, J., "Immune response following introcular delivery of recombinant viral vectors", Gene Therapy, 10:977-982, 2003.
National Institutes of Health Recombinant DNA Advisory Committee (RAC Meeting) Sep. 6-7, 2001, Meeting Agenda, Human Gene Therapy 12:2021-2032, Nov. 1, 2001.
Mashhour, B. et al., "In vivo adenovirus-mediated gene transfer into ocular tissues", Gene Therapy, 1:122-126, 1994.
Li, T. et al., "In Vivo Transfer of a Reporter Gene to the Retina Mediated by an Adenoviral Vector", Investigative Ophthalmology & Visual Science, 35(5):2543-2549, Apr. 1994.
Jomary, C. et al., "Adenovirus-mediated gene transfer to murine retinal cells in vitro and in vivo", FEBS Letters, 347:117-122, 1994.
Bennett, J. et al., "Adenovirus Vector-Mediated In Vivo Gene Transfer Into Adult Murine Retina", Investigative Ophthalmology & Visual Science, 35(5):2535-2542, 1994.
Mahasreshti, P.J. et al., "Adenovirus-mediated Soluble FLT-1 Gene Therapy for Ovarian Carcinoma", Clinical Cancer Research, 7:2057-2066, Jul. 2001.
Dejneka, NS et al., "Pharmacologically regulated gene expression in the retinal following transduction with viral vectors", Gene Therapy, 8:442-446, 2001.
Cunningham, S.A. et al., "Identification of the Extracellular Domains of Flt-1 That Mediate Ligand Interactions", Biochemical and Biophysical Research Communications 231:596-599, 1997.
Harris, Adrian L., "von Hippel-Lindau Syndrome: Target for Anti-Vascular Endothelial Growth Factor (VEGF) Receptor Therapy", The Oncologist, 5(suppl 1):32-36, 2000.
Weismann, C. et al., "Crystal Structure at 1.7 A Resolution of VEGF in Complex with Domain 2 of the Flt-1 Receptor", Cell, 91:695-704, Nov. 28, 1997.
Bainbridge, JWB et al., "Inhibition of retinal neovascularisation by gene transfer of soluble VEGF receptor sFlt-1", Gene Therapy, 9:320-326, 2002.
Gerber, Hans-Peter et al., "Complete Inhibition of Rhabdomyosarcoma Xenograft Growth and Neovascularization Requires Blockade of Both Tumor and Host Vascular Endothelial Growth Factor", Cancer Research, 60:6253-6258, Nov. 15, 2000.
Hu, Shi-zhen et al., "Minibody: A Novel Engineered Anti-Carcinoembryonic Antigen Antibody Fragment (Single-Chain Fv-CH3) Which Exhibits Rapid, High-Level Targeting of Xenografts", Cancer Research, 56:3055-3061, Jul. 1, 1996.
Lai, Chooi-May et al., "Long-Term Evaluation of AAV-Mediated sFlt-1 Gene Therapy for Ocular Neovascularization in Mice and Monkeys", Molecular Therapy, 12(4):659-668, Oct. 2005.
Li, Erqiu et al., "Mammalian cell expression of dimeric small immune proteins (SIP)", Protein Engineering, 10:(6):731-736, 1997.
Thompson, Jerry et al., "Improved binding of a bivalent single-chain immunotoxin results in increased efficacy for in vivo T-cell depletion", Protein Engineering, 14(12):1035-1041, 2001.
Kendall, R.L. and Thomas, K.A., "Inhibition of vascular endothelial cell growth factor activity by an endogenously encoded soluble receptor", Proc. Natl. Acad. Sci. USA, 90:10705-10709, Nov. 1993.
Holash, J. et al., "VEGF-Trap: A VEGF blocker with potent antitumor effects", Proceeding of the National Academy of Sciences of USA, 99(17):11393-11398, Aug. 20, 2002.
Vangelista, L. et al., "A minimal receptor-Ig chimera of human FcepsilonRI alpha-chain efficiently binds secretory and membrane IgE", Protein Engineering, 15(1):51-57, Jan. 2002.
Olafsen, T. et al., "Characterization of engineered anti-p185HER-2 (scFv-CH3) 2 antibody fragments (minibodies) for tumor targeting", Protein Engineering Design & Selection, 17(4):315-323, Apr. 2004.
Hu, S-Z et al., "Minibody: A Novel Engineered Anti-Carcinoembryonic Antigen Antibody Fragment (Single-chain FV-CH3) which Exhibits Rapid, High-Level Targeting of Xenografts", Cancer Research, 56(13):3055-3061, Jul. 1, 1996.
Afanasieva T.A. et al., "Single-chain antibody and its derivatives directed against vascular endothelial growth factor: application for antiangiogenic gene therapy", Gene Therapy, 10(21):1850-1859, Oct. 1, 2003.
Supplementary Partial European Search Report—European patent application No. EP 05 81 0409, 2008.

\* cited by examiner

A

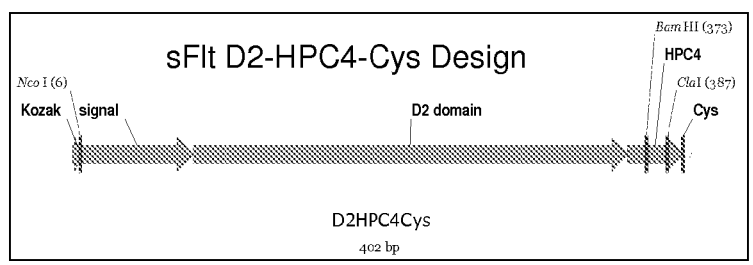

B gccaccatggtcagctactgggacaccggggtcctg
ctgtgcgcgctgctcagctgtctgcttctcacaggatct
ggtagacctttcgtagagatgtacagtgaaatccccg
aaattatacacatgactgaaggaagggagctcgtca
ttccctgccggttacgtcacctaacatcactgttacttt
aaaaaagtttccacttgacactttgatccctgatggaa
aacgcataatctgggacagtagaaagggcttcatca
tatcaaatgcaacgtacaaagaaatagggcttctga
cctgtgaagcaacagtcaatgggcatttgtataagac
aaactatctcacacatcgacaaaccgaagatcaagt
ggatccacgcctcatcgatggcaaatgctga 402 basepairs

MVSYWDTGVLLCALLSCLLLTG
SGRPFVEMYSEIPEIIHMTEGRE
LVIPCRVTSPNITVTLKKFPLDTL
IPDGKRIIWDSRKGFIISNATYKE
IGLLTCEATVNGHLYKTNYLTH
RQTEDQVDPRLIDGKC*

108 amino acids (mature)

FIGURE 2

VEGF ANTAGONIST COMPOSITIONS AND USES THEREOF

CROSS REFERENCE TO RELATED APPLICATIONS

This is a national stage application of PCT International Application PCT/US11/46802, filed Aug. 5, 2011, that claims priority to U.S. Provisional Patent Application 61/371,546, filed Aug. 6, 2010, both of which are incorporated by reference herein in their entirety.

FIELD OF THE INVENTION

The invention relates to compositions and methods for treating a disease or disorder associated with vascular endothelial growth factor (VEGF). Specifically, the invention relates to an oligomerized VEGF binding domains to provide VEGF antagonism, and thereby treat diseases associated thereof.

BACKGROUND OF THE INVENTION

VEGF is a potent angiogenic and vascular permeability enhancing factor. VEGF may contribute to osteoarthritis ("OA") pain and cartilage and bone structural changes by: 1) enhancing synovial inflammation, effusion, and angiogenesis, 2) promoting blood vessel invasion into cartilage, 3) contributing to bone marrow edema, 4) promoting local re-initiation of endochondral bone formation, resulting in tidemark duplication, bone sclerosis, chondrocyte hypertrophy, and cartilage thinning. It is likely therefore that blocking VEGF signaling is of benefit to relieve OA pain and/or to protect joint structure. It is known that VEGF is upregulated in human and animal models of OA and can be restored to normal levels in vivo by intra-articular treatment with a known analgesic agent. Recent findings also indicated that VEGF/KDR signaling may be up-regulated in OA, and cartilage and synovium are among the sources for VEGF over-expression under pathological conditions. Additionally, it was demonstrated that increasing VEGF expression by overexpressing its upstream regulator hypoxia inducible factor alpha (Hif1a) in human synovial and chondrocyte cell cultures results in a substantial increase in cyclooxygenase-2 (COX-2) expression, which may be an indication of a painful stimulus. In animal models of OA, a significant correlation (r=0.437, p=0.008) was identified between levels of synovial fluid VEGF and prostaglandin E2 (PGE2), a neuronal sensitizing agent generated by cyclooxygenases, including COX-2, that has been used as a marker for pain in joints. Further, blocking VEGF in animal models of OA results in decreased synovial inflammation and hyperplasia, two factors correlated with OA pain in humans. Longer half lives of protein based inhibitors will be necessary to make this a viable therapeutic strategy. Multiple sustained release formulation efforts have been attempted, but all resulted in marked protein instability at specific locations in the protein sequence.

Accordingly, there exists a need for improved VEGF antagonist compositions so as to improve their stability, half lives, and other beneficial characteristics.

SUMMARY OF THE INVENTION

The invention provides a VEGF antagonist oligomer having a plurality of monomers, each monomer having the second VEGF binding domain (D2) of FMS-like tyrosine kinase-1 (FLT-1). The oligomer exhibits higher stability and longer half-life, relative to FLT-1. Furthermore, the oligomer enhances the affinity of VEGF binding, and thereby antagonizes the binding of VEGF to FLT-1. In some embodiments, the monomers in the oligomer are operably linked to each other on a multiarm poly-ethylene glycol (PEG).

Additionally, the invention provides methods for producing the VEGF antagonist oligomer. In some embodiments, the oligomers are produced by copper oxidation.

The invention also provides pharmaceutical compositions that comprise a therapeutically effective amount of the VEGF antagonist oligomer.

The invention further provides kits that comprise a therapeutically effective amount of the VEGF antagonist oligomer.

The invention further provides methods for treating a disease or disorder associated with or otherwise caused by the interaction between VEGF and its receptor, in a subject, by administering a therapeutically effective amount of the VEGF antagonist oligomer.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) can be obtained from the Office upon request and payment of the necessary fee.

FIG. 2 shows (a) an expression construct; and (b) a nucleic acid (SEQ ID NO:4) as well as amino acid (SEQ ID NO:3) sequences of the construct.

FIG. 11 shows the stability of D2 dimer relative to sFLT01 at elevated temperatures: (a) sFLT1; (b) D2 Dimer; and (c) sFLT1+D2 Dimer.

FIG. 12: VEGF binding assay showing that the dimer retained at least 50% activity after 56 days. The EC50 value for sFLT01 was comparable to those obtained previously, but the D2 dimer typically shows a 2-fold higher EC50 (8-10 pM).

FIG. 13 shows accumulation of ~30 kDa and ~10 kDa cleavage products and three higher MW aggregates in the sFLT01 preparation, while D2 showed a small amount of ~10 kDa cleavage product and a modest amount of a higher MW aggregate band running near the mobility expected for unreduced dimer (FIG. 13, left panel)

FIG. 14 shows the effect of the incubation on the activity (1/EC50) relative to time zero.

FIG. 15 shows VEGF assay for (a) sFLT1 and (b) D2 dimer. After only 14 days, there was a significant difference in activity between D2 dimer and sFLT01, sFLT01 having lost ~30% activity while the D2 dimer <10%. After 28 days, the rate of decline slowed for both sFLT01 and D2, producing similar overall activity for both after 56 days. After 94 days, the D2 activity appeared to increase, likely due to evaporative concentration of the sample.

DETAILED DESCRIPTION OF THE INVENTION

The invention relates to compositions and methods for treating a disease or disorder associated with or otherwise caused by the interaction between vascular endothelial growth factor (VEGF) and its receptor (e.g., FLT-1). Specifically, the invention relates to an oligomerized VEGF binding domains to provide VEGF antagonism, and thereby treat diseases associated thereof.

In one embodiment, provided herein is a VEGF antagonist oligomer comprising a plurality of monomers operably linked to each other, wherein each monomer comprises the second VEGF binding domain (D2) of FLT-1.

In another embodiment, provided herein is a method for producing a VEGF antagonist oligomer, the method comprising: culturing a host cell; recovering a plurality of monomers from said host cell, wherein each monomer comprises the second VEGF binding domain (D2) of FLT-1; and linking said plurality of monomers.

In yet another embodiment, provided herein is a pharmaceutical composition comprising: a therapeutically effective amount of a VEGF antagonist oligomer, said oligomer comprising: a plurality of monomers operably linked to each other, wherein each monomer comprises the second VEGF binding domain (D2) of FLT-1.

In further embodiment, provided herein is a method for treating a disease or disorder associated with or otherwise caused by the interaction between VEGF and its receptor, in a subject, the method comprising: administering to said subject a therapeutically effective amount of a VEGF antagonist oligomer, said oligomer comprising a plurality of monomers operably linked to each other, wherein each monomer comprises the second VEGF binding domain (D2) of FLT-1.

VEGF is a key driver of pathologic disorders of angiogenesis and vascular permeability, and has recently been implicated in perpetuation of certain chronic pain conditions. Soluble receptor-based inhibitors, delivered as either genes or proteins, can be effective at ameliorating some of the pathologic effects of chronic VEGF over-expression, but protein forms of these soluble receptors suffer therapeutically from relatively short half lives. Sustained release preparations of these inhibitors would be desirable for long term therapeutic intervention in chronic conditions, but maintenance of protein stability using full size soluble receptor/immunoglobulin fusion constructs is challenging. The inventors of the instant application surprisingly and unexpectedly found that an oligomerized form of the second VEGF binding domain (D2) of FMS-like tyrosine kinase-1 (FLT-1) (e.g., a dimerized form of D2) is suitable for providing sustained VEGF antagonism to treat chronic pain and vascular permeability/angiogenesis disorders while offering protein stability under sustained release conditions. The oligomer exhibits higher stability and longer half-life, relative to FLT-1. Specifically, the oligomer exhibits bioactivity comparable to full size sFlt soluble receptor constructs, and is stable under accelerated stability conditions for at least 3 months. Furthermore, the oligomer enhances the affinity of VEGF binding, and thereby antagonizes the binding effect of VEGF to FLT-1.

In one embodiment, the second VEGF binding domain (D2) of the invention comprises the amino acid sequence set forth in SEQ ID NO: 1. In another embodiment, the second VEGF binding domain (D2) comprises a homolog, a variant, or a functional fragment of SEQ ID NO: 1. In another embodiment, the second VEGF binding domain (D2) comprises an amino acid sequence that is about 60%, 65%, 70%, 75%, 80%, 85%, 90%, or 95% identical to SEQ ID NO:1. In another embodiment, the second VEGF binding domain (D2) comprises a fragment of the amino acid sequence of SEQ ID NO:1. The fragment may comprise one or more functional regions. Each possibility represents a separate embodiment of the present invention.

In one embodiment, the second VEGF binding domain (D2) is encoded by the nucleic acid sequence set forth in SEQ ID NO: 2. In another embodiment, the second VEGF binding domain (D2) nucleic acid sequence comprises a homolog, a variant, or a functional fragment of SEQ ID NO: 2. In another embodiment, the second VEGF binding domain (D2) is encoded by a nucleic acid sequence that is about 60%, 65%, 70%, 75%, 80%, 85%, 90%, or 95% identical to SEQ ID NO:2. In another embodiment, the second VEGF binding domain (D2) is encoded by a fragment of a nucleic acid sequence set forth in SEQ ID NO:2. The fragment may comprise one or more functional regions. Each possibility represents a separate embodiment of the present invention.

Figure 1:
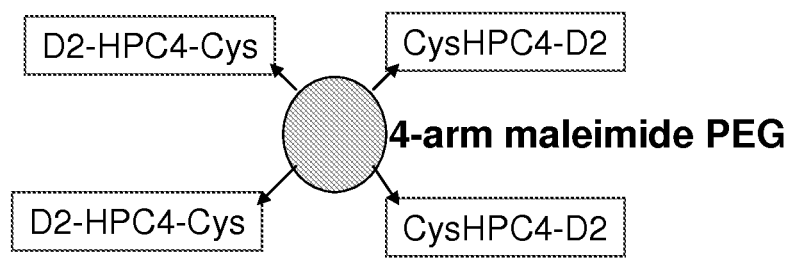
FIG. 1 illustrates a concept of oligomerizing the VEGFR D2 domain on a multiarm PEG to obtain high affinity VEGF binding.
Figure 3:
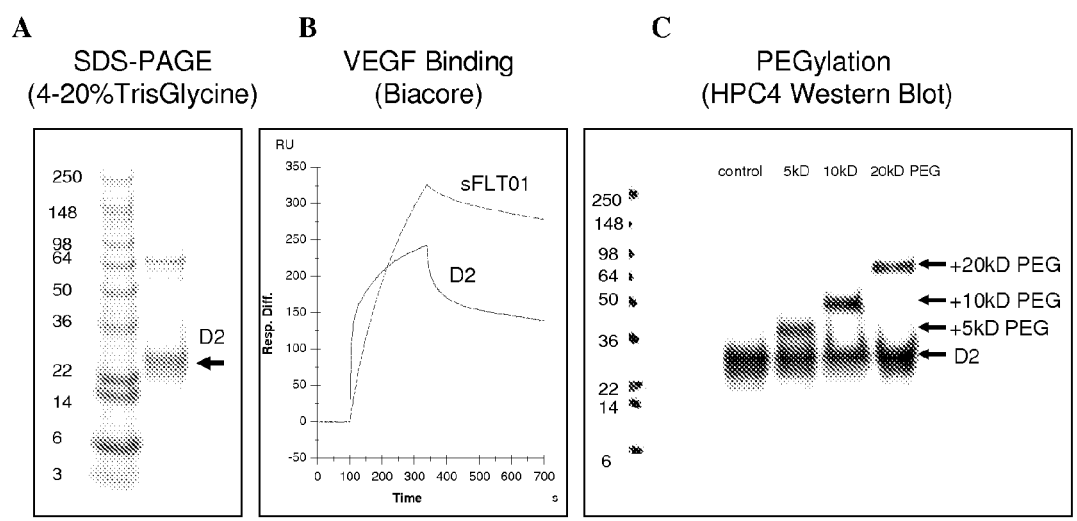
FIG. 3 shows (a) SDS-PAGE of the D2 domain; (b) the D2-Cys protein bound to immobilized VEGF on a Biacore surface (5 µg/ml protein in HBS-EP); and (c) Western blot using HPC4 Ab showing that in addition to unreacted D2, the presence of a single higher MW product, indicating that the protein can be monoPEGylated with various size PEGs.
Figure 4:
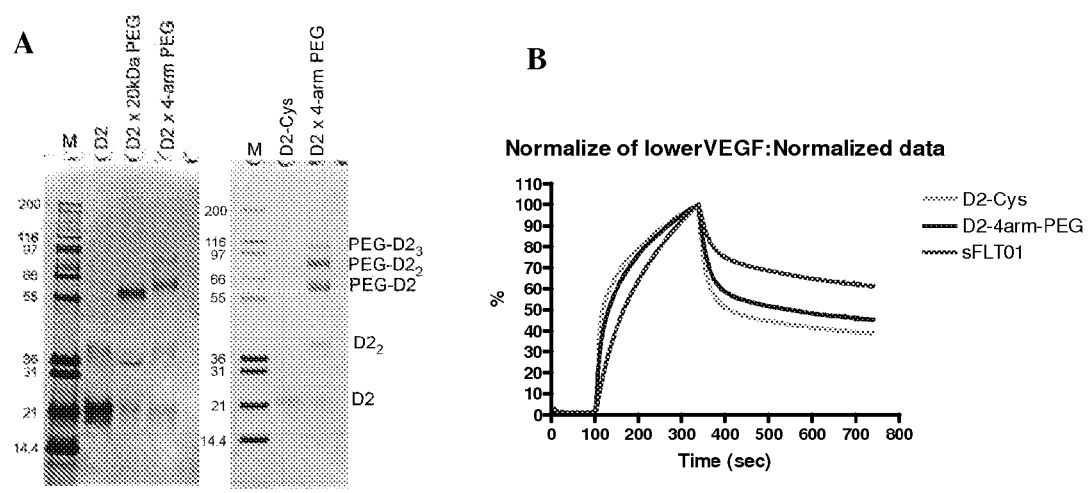
FIG. 4: (a) SDS PAGE showed the presence of a ~60 kDa (apparent MW) product migrating near the product obtained with a linear 20 kDa PEG as well as faint bands having mobilities consistent with multiple D2 on each 4-arm PEG; and (b) the normalized sensorgram off the low-level VEGF chip.

The domains utilized may consist of the entire second VEGF binding domain (D2) of FLT-1 or they may consist of mutants or fragments thereof that maintain the ability to inhibit the activity of the agonistic complex VEGF/FLT-1.

FLT-1 is a well known protein. The amino acid and nucleic acid sequences of FLT-1 are well known in the art. For example, GenBank Identification Numbers AAC16449 and AF063657 contain FLT-1 amino acid and nucleic acid sequences, respectively.

A monomer of the invention may include the sequence of the second VEGF binding domain (D2), a signal sequence, a linker sequence, or other sequences relating to expression and purification of monomers. In one example, a monomer of the invention may include the sequence of expression vector shown in FIG. 2A.

An oligomer of the invention may include a plurality of monomers. The oligomer may include any number of monomers, depending on the need. In one embodiment, the oligomer is a dimer. In another embodiment, the oligomer is a trimer. In yet another embodiment, the oligomer is a tetramer. Other forms of oligomers are also encompassed within the scope of the invention.

The monomers in the oligomer may be operably linked to each other through any known linking method. For example, two or more monomers may be operably linked through a simple covalent bond, a flexible peptide linker, a disulfide bridge or a polymer such as polyethylene glycol (PEG). Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by recombinant expression, wherein the nucleic acid sequence encoding the monomer contains one or more cysteine encoding codons. Linking through polyethylene glycols (PEG) can be achieved by reaction of monomers having free cysteines with multifunctional PEGs, such as linear bis-maleimide PEGs. Alternatively, linking can be performed though the glycans on the D2 monomer after their oxidation to aldehyde form and using multifunctional PEGs containing aldehyde-reactive groups.

In some embodiments, at least one of monomers is PEGylated or chemically modified to another form. PEGylation of the molecules can be carried out, e.g., according to the methods described in Youngster et al., Curr Pharm Des (2002), 8:2139; Grace et al., J Interferon Cytokine Res (2001), 21:1103; Pepinsky et al., J Pharmacol Exp Ther (2001), 297:1059; Pettit et al., J Biol Chem (1997), 272:2312; Goodson et al. Biotechnology NY (1990), 8:343; Katre; J Immunol (1990), 144:209, Behrens et al US2006/0198819 A1, Klausen et al US2005/0113565 A1.

Any kind of polyethylene glycol is suitable for the present invention provided that the PEG-polypeptide-oligomer is still capable of antagonizing or neutralizing the interaction between VEGF and FLT-1 which can be assayed according to methods known in the art.

Preferably, the polyethylene glycol of the polypeptide-dimer of the present invention is PEG 1000, 2000, 3000, 5000, 10000, 15000, 20000 or 40000 with PEG 20000 or 40000 being particularly preferred.

In one example, the oligomer is a tetramer that comprises four FLT-1 D2 domains on a multiarm PEG, as shown in FIG. 1, to obtain high affinity of VEGF binding while providing for enhanced PK properties by the use of the linked PEG.

The oligomer of the present invention are preferably recombinantly produced by use of a polynucleotide encoding a monomer of the oligomer and vectors, preferably expression vectors containing said polynucleotides. For the production of the oligomers of the invention, the polynucleotides are obtained from existing clones, i.e., preferably encode the naturally occurring polypeptide or a part thereof. Polypeptides encoded by any polynucleotide which hybridises to the complement of the native DNA or RNA under highly stringent or moderate stringent conditions (for definitions, see Sambrook, Molecular Cloning A Laboratory Manual, Cold Spring Harbor Laboratory (1989) N.Y.) as long as that polypeptide maintains the biological activity of the native sequence, are also useful for producing the oligomers of the present invention.

The recombinant vectors can be constructed according to methods well known to the person skilled in the art; see, e.g., Sambrook, Molecular Cloning A Laboratory Manual, Cold Spring Harbor Laboratory (1989) N.Y. A variety of expression vector/host systems may be utilized to contain and express sequences encoding the oligomers of the present invention.

Exemplary vectors include plasmids, phagemids, cosmids, viruses and phage nucleic acids or other nucleic acid molecules that are capable of replication in a prokaryotic or eukaryotic host. The vectors typically contain a marker to provide a phenotypic trait for selection of transformed hosts such as conferring resistance to antibiotics such as ampicillin or neomycin The vector may be an expression vector, wherein the nucleic acid encoding the antibody is operably linked to an expression control sequence. Typical expression vectors contain transcription and translation terminators, initiation sequences, and promoters useful for regulation of the expression of the nucleic acid molecules of the invention. The vectors may also contain genetic expression cassettes containing an independent terminator sequence, sequences permitting replication of the vector in both eukaryotes and prokaryotes, i.e., shuttle vectors and selection markers for both prokaryotic and eukaryotic systems.

Suitable promoters include constitutive promoters and inducible promoters. Representative expression control sequences/promoters include the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of yeast alpha mating factors, promoters derived from the human cytomegalovirus, metallothionine promoter, murine mammary tumor virus promoter, Rous sarcoma virus promoter, polyhedrin promoter and promoters derived from polyoma, adenovirus, retrovirus, and simian virus, e.g., the early and late promoters of SV40.

The invention also includes non-human hosts such as cells or organisms containing a nucleic acid molecule or a vector of the invention. By "host" it is meant a non-human unicellular or multicellular organism or a "host cell", which refers to a cell or population of cells into which a nucleic acid molecule or vector of the invention is introduced. "A population of host cells" refers to a group of cultured cells into which a nucleic acid molecule or vector of the present invention can be introduced and expressed.

A host of the present invention may be prokaryotic or eukaryotic. Suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas*, *Bacillus*, such as *Bacillus subtilis*, and *Streptomyces*. Suitable eukaryotic cells include yeast and other fungi, insect cells, plant cells, human cells, and animal cells, including mammalian cells, such as hybridoma lines, COS cells, NS0 cells and CHO cells.

The invention also includes methods of producing a VEGF antagonist oligomer, the method comprising: culturing a host cell; and recovering a plurality of monomers from said host cell, wherein each monomer comprises the second VEGF binding domain (D2) of FMS-like tyrosine kinase-1 (FLT-1).

Depending on the expression system and host selected, the monomer molecules are produced by growing host cells transformed by an expression vector described above whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art. For example, once expressed, the product may be isolated and purified by any number of techniques, well known in the art. A protein (e.g., monomer) of the present invention obtained as above may be isolated from the interior or exterior (e.g., medium) of the cells or hosts, and purified as a substantially pure homogeneous protein. The method for protein isolation and purification is not limited to any specific method. In fact, any standard method may be used. For instance, column chromatography, filtration, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

For chromatography, for example, affinity chromatography, ion-exchange chromatography, hydrophobic chromatography, gel filtration, reverse phase chromatography, adsorption chromatography, and such may be used (ed. Daniel R. Marshak et al. (1996) Strategies for Protein Purification and Characterization: A Laboratory Course Manual., Cold Spring Harbor Laboratory Press). These chromatographies may be performed by liquid chromatography, such as, HPLC and FPLC. Thus, the present invention provides highly purified proteins produced by the above methods.

The invention also provides a pharmaceutical composition comprising the oligomer, nucleic acid, vector, or host cell of this invention and one or more pharmaceutically acceptable carriers. "Pharmaceutically acceptable carriers" include any excipient which is nontoxic to the cell or mammal being exposed thereto at the dosages and concentrations employed. The pharmaceutical composition may include one or additional therapeutic agents.

Pharmaceutically acceptable carriers include solvents, dispersion media, buffers, coatings, antibacterial and antifungal agents, wetting agents, preservatives, buggers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

The pharmaceutical compositions of the invention may be formulated in a variety of ways, including for example, liquid, semi-solid and solid dosage forms, such as liquid solutions (e.g., injectable and infusible solutions), dispersions or suspensions, tablets, pills, powders, liposomes and suppositories. In some embodiments, the compositions are in the form of injectable or infusible solutions. The composition is in a form suitable for oral, intravenous, intraarterial, intramuscular, subcutaneous, parenteral, transmucosal, transdermal, or topical administration. The composition may be formulated as an immediate, controlled, extended or delayed release composition.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

In some embodiments, the composition includes isotonic agents, for example, sugars, polyalcohols, such as mannitol, sorbitol, or sodium chloride. Prolonged absorption of the injectable compositions can be brought about by including in the composition an agent which delays absorption, for example, aluminum monostearate and gelatin.

Sterile injectable solutions can be prepared by incorporating the molecule, by itself or in combination with other active agents, in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in US Appl. Publ. No. 2002/0102208 A1, which is incorporated herein by reference in its entirety. Such articles of manufacture will preferably have labels or package inserts indicating that the associated compositions are useful for treating a subject suffering from, or predisposed to autoimmune or neoplastic disorders.

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

The invention further provides methods of treating a disease or condition, comprising administering to a mammal in need thereof a therapeutically effective amount of a VEGF antagonist oligomer.

In one embodiment, provided herein is a method for treating a disease or disorder caused by or otherwise associated with the binding of VEGF to its receptor (e.g., FLT-1), in a subject, the method comprising: administering to said subject a therapeutically effective amount of a VEGF antagonist oligomer, said oligomer comprising a plurality of monomers operably linked to each other, wherein each monomer comprises the second VEGF binding domain (D2) of FLT-1.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

Examples of disease or disorder caused by or otherwise associated with the binding of VEGF to its receptor, include, but are not limited to, a chronic pain, a pathologic angiogenesis, a cancer, a myocardial angiogenesis, and a vascular permeability disorder.

The VEGF antagonist oligomer may be administered alone, or in combination with one or more therapeutically effective agents or treatments. The other therapeutically effective agent may be conjugated to the VEGF antagonist oligomer, incorporated into the same composition as the VEGF antagonist oligomer, or may be administered as a separate composition. The other therapeutically agent or treatment may be administered prior to, during and/or after the administration of the VEGF antagonist oligomer.

The administration of the VEGF antagonist oligomer with other agents and/or treatments may occur simultaneously, or separately, via the same or different route, at the same or different times. Dosage regimens may be adjusted to provide the optimum desired response (e.g., a therapeutic or prophylactic response).

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The composition of the invention may be administered only once, or it may be administered multiple times. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets). Administration to a host may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

The composition of the invention (e.g., VEGF antagonist oligomer) may be administered parenterally (e.g., intravenous, subcutaneous, intraperitoneal, intramuscular). Further, the composition of the invention may be administered by intravenous infusion or injection. The composition of the invention may be administered by intramuscular or subcutaneous injection. In some embodiments, the composition of the invention may be administered orally. As used herein, a "composition" refers to any composition that contains a pharmaceutically effective amount of a VEGF antagonist oligomer.

The methods of treatment described herein can be used to treat any suitable mammal, including primates, such as monkeys and humans, horses, cows, cats, dogs, rabbits, and rodents such as rats and mice. In one embodiment, the mammal to be treated is human.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

Oligomerized Form of the VEGF Binding Domain of FLT-1

To overcome stability issues, the invention is an oligomerized form, including a dimerized form of D2, the VEGF binding domain of fms-like tyrosine kinase-1 (Flt-1) to provide VEGF antagonism to treat chronic pain and vascular permeability/angiogenesis disorders. This construct overcomes the protein stability issues inherent in sustained release formulation procedures and allows for effective use as a stable and effective therapeutic for chronic disorders, the pathophysiologic manifestations of which are primarily driven by VEGF.

Figure 5:
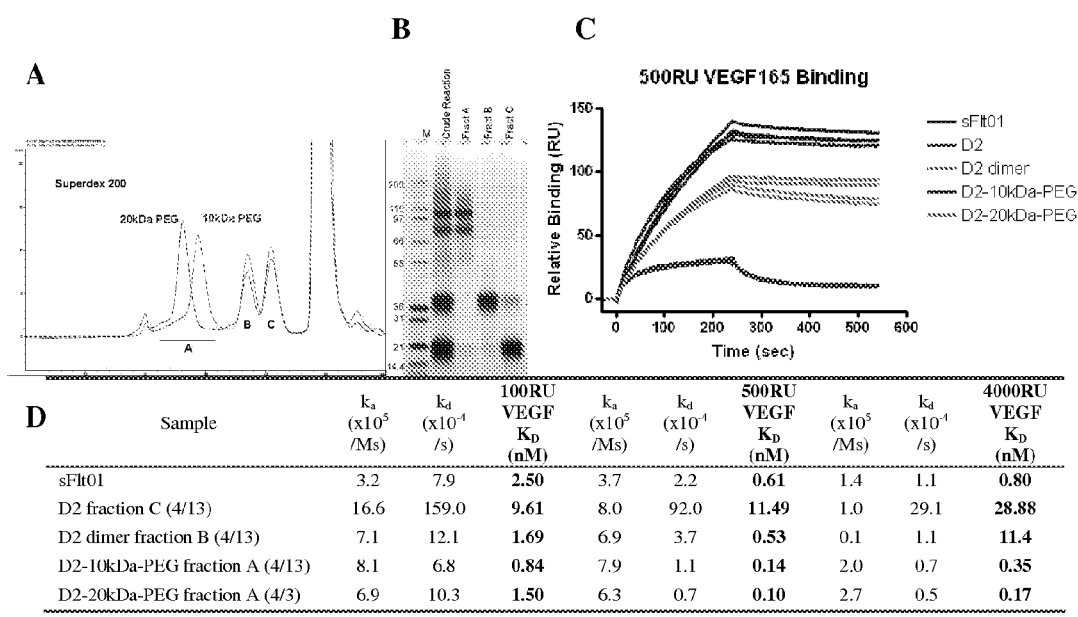
FIG. 5: The D2 domain with the HPC4 tag and C-terminal cysteine was found to spontaneously form disulfide-linked dimer as a side product in PEGylation reactions. When SEC-purified from reactions or conditioned medium (FIGS. 5a and b), the dimer bound VEGF165 with similar or higher affinity than sFLT01 by Biacore (FIGS. 5c and d).
Figure 6:
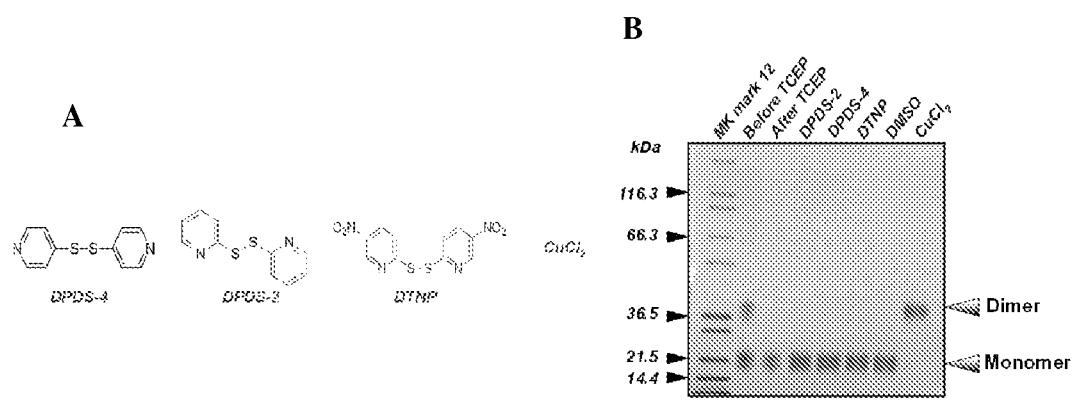
FIG. 6: A panel of reagents was tested for the ability to dimerize D2 obtained from transient expression. Briefly, protein (in PBS) was treated with 2 mM TCEP, buffer exchanged into PBS and reacted 0.5 eq of either pyridyl disulfide reagents or 5 mM $CuCl_2$ (FIG. 6a) for 1 h at 25° C. SDS PAGE of the products is shown in FIG. 6b. TCEP effectively reduced the dimer disulfide yielding monomeric D2 running as a doublet at ~20 kDa.
Figure 7:
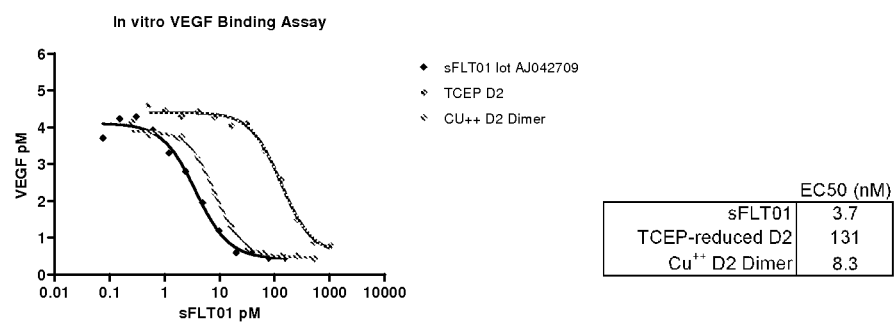
FIG. 7 shows the results of in vitro VEGF binding assay.
Figure 9:
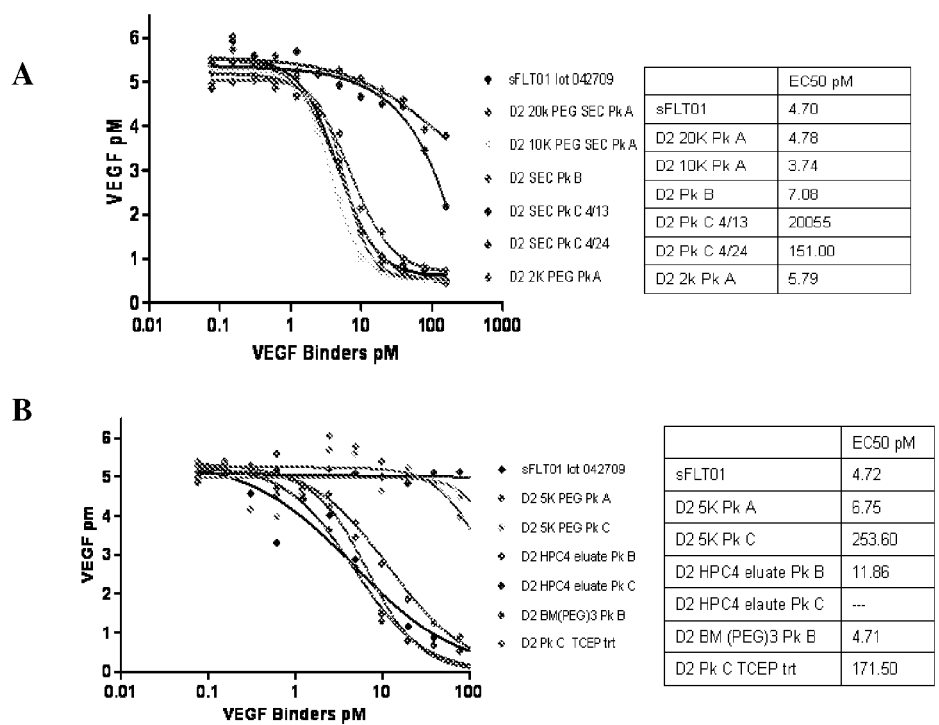
FIG. 9 *a* and *b*: PEG-linked D2 dimers linked by 0.6, 2, or 5 kDa linkers and purified by SEC ("D2 BM(PEG)3 PkB", "D2 2k Pk A", "D2 5K Pk A" respectively) have a binding affinity to VEGF165 comparable to sFLT01 while disulfide linked dimers ("D2 HPC4 eluate Pk B", D2 Pk B") show slightly weaker binding (these were not copper-oxidized).

Higher potency, longer PK, or better targeting/biodistribution are desired for product differentiation in the crowded VEGF antagonist field. A potentially useful approach would be to oligomerize the VEGFR D2 domain on a multiarm PEG to obtain high affinity VEGF binding while providing for enhanced PK properties by the use of the linked PEG. The MW of the D2 domain is only 12.3 kDa. The concept is illustrated in FIG. 1.

The nucleotides with Kozak sequence and signal peptide sequence was synthesized and Gateway-cloned into pCEP4 (−E+I)DEST vector and transfected into HEK293-EBNA cells for expression. The protein was purified over a HPC4 Ab affinity column and characterized by SDS-PAGE, Biacore VEGF binding and by PEGylation.

By Western analysis, as shown in FIG. 3, the product appeared to be predominantly a single band (FIG. 3*c*). Occasionally, a higher MW band appeared upon sample manipulation possibly due to oxidation (FIG. 3*a*). The D2-Cys protein bound to immobilized VEGF on a Biacore surface (FIG. 3*b*, 5 μg/ml protein in HBS-EP). The affinity is lower than sFLT01 (D2-9Gly-Fc) mainly due to a slower off rate as expected from the lack of affinity in the monomeric form. To test for the presence of a reactive cysteine, the D2-Cys sample was briefly treated with TCEP beads and then reacted with maleimide PEG (100 uM PEG, 2 hours at room temperature). Western blot using HPC4 Ab showed in addition to unreacted D2, the presence of a single higher MW product, indicating that the protein can be monoPEGylated with various size PEGs, presumably via the free Cys at its C-terminus To determine if the D2 domain could form oligomeric structures on a 4-arm 20 kDa maleimide PEG, 23 ug of the purified D2-Cys construct in HPC4 column elution buffer was treated with immoblized TCEP, allowed to air oxidize for 30', and then reacted at 0.33 mol PEG per mol D2 overnight at 25° C. SDS PAGE showed the presence of a ~60 kDa (apparent MW) product migrating near the product obtained with a linear 20 kDa PEG as well as faint bands having mobilities consistent with multiple D2 on each 4-arm PEG (FIG. 4*a*). In a second experiment, the initial reduction and coupling were performed on a sample first concentrated by Amicon ultrafiltration. This showed consumption of almost all of the D2-cys with approximately eqimolar amounts of products migrating at ~60 kDa and ~80 kDa, presumably D2-PEG and $(D2)_2$-PEG (middle panel below—the provisional assignments of each species is shown). Biacore analysis was then performed on the crude reaction products. The normalized sensorgram for a low-level immobilized VEGF chip is shown in FIG. 4*b*. These data show the presence of a higher affinity component in the PEGylation reaction products compared to D2.

Example 2

Dimerizaton of the VEGF Binding Domain of FLT-1

A panel of reagents was tested for the ability to dimerize D2 obtained from transient expression. Briefly, protein (in PBS) was treated with 2 mM TCEP, buffer exchanged into PBS and reacted 0.5 eq of either pyridyl disulfide reagents or 5 mM $CuCl_2$ (FIG. 6*a*) for 1 h at 25° C. SDS PAGE of the products is shown below (FIG. 6*b*). TCEP effectively reduced the dimer disulfide yielding monomeric D2 running as a doublet at ~20 kDa. The reduced product was desalted and reacted with a panel of potential dimerization reagents (FIG. 6). None of the pyridyl disulfide reagents was effective in regenerating the dimer, but $CuCl_2$ produced quantitative oxidation to dimer after 1 h. A titration experiment with decreasing amounts of copper in 20 mM Tris pH7.4 showed that 100 uM $CuCl_2$ was sufficient.

Dimer was prepared using 100 uM $CuCl_2$ and the products assayed for VEGF binding activity by competitive VEGF ELISA. The results of the ELISA are shown in FIG. 7. The TCEP-reduced D2 monomer showed ~35-fold higher EC50 as sFLT01 whereas the Cu-oxidized dimer showed 2.2-fold higher EC50 than sFLT01. This value was similar to that obtained for dimers obtained without copper oxidation (FIG. 5). This molecule lacks the hinge region and Fc domain of sFLT01 and represents a minimal high affinity VEGF binding entity. Its low MW may provide advantages in localized delivery, including higher diffusion through tissue, more rapid systemic clearance thus reducing potential side effects of VEGF antagonism, and greater stability upon formulation into slow-release depots.

The D2 domain with the HPC4 tag and C-terminal cysteine was also found to spontaneously form disulfide-linked dimers after partial reduction. These dimers, purified by SEC from PEGylation reactions or conditioned medium (FIGS. 5*a* and *b*), bound VEGF165 with similar or higher affinity to VEGF than sFLT01 by Biacore (FIGS. 5*c* and *d*).

Dimers wherein two D2 domains of sFLT are coupled via PEG linkers were prepared by reaction of the partially-reduced monomer with homobifunctional PEGs. Products were isolated by SEC (FIG. 5) and analyzed for VEGF binding affinity using competitive ELISA (FIG. 9). VEGF165 binding of three SEC purified D2 domain constructs including dimers prepared with 0.6, 2 and 5 kDa linkers and as well as the 10 and 20 kDa 4-arm PEG conjugates as described in Example 1 was determined. The assay was performed by binding to 10 pM recombinant VEGF (R&D Systems) in phosphate-buffered saline. The sample concentrations ranged from 0.0763 to 156 pM. Following binding, the free VEGF concentration was determined by a VEGF-specific ELISA (R&D Systems). As shown in FIG. 9, PEG-linked D2 dimers linked by 0.6, 2, or 5 kDa linkers and purified by SEC ("D2 BM(PEG)3 PkB", "D2 2k Pk A", "D2 5K Pk A" respectively) showed a binding affinity to VEGF165 comparable to sFLT01 while disulfide linked dimers ("D2 HPC4 eluate Pk B", D2 Pk B") showed slightly weaker binding. Four-arm D2 tetramers linked with 4-arm PEGs of either 10 kDa or 20 kDa ("D2 10K Pk A", "D2 20K Pk A") also showed equivalent binding as sFLT01. D2 monomer purified directly from medium ("D2 HPC4 eluate Pk C") had no detectable binding to VEGF165. SDS PAGE showed the protein in this sample was intact. Reduced D2 monomers isolated from PEGylation reactions ("D2 Pk C 4/13", "D2 Pk C 4/24", "D2 5K Pk C") or D2 (mixture of monomer and dimer) which had been freshly treated with TCEP and desalted ("D2 Pk C TCEP trt") showed <3% of the binding affinity of sFLT01. These results were comparable to Biacore data (FIG. 5) except for the 4-arm PEG conjugates, which showed higher affinity than sFLT01 by Biacore than by VEGF ELISA. Biacore also showed weak binding of the D2 monomer from conditioned medium (~10 nM Kd) at higher concentrations than those assayed with the VEGF ELISA.

Example 3

Stability of Dimer

Figure 8:
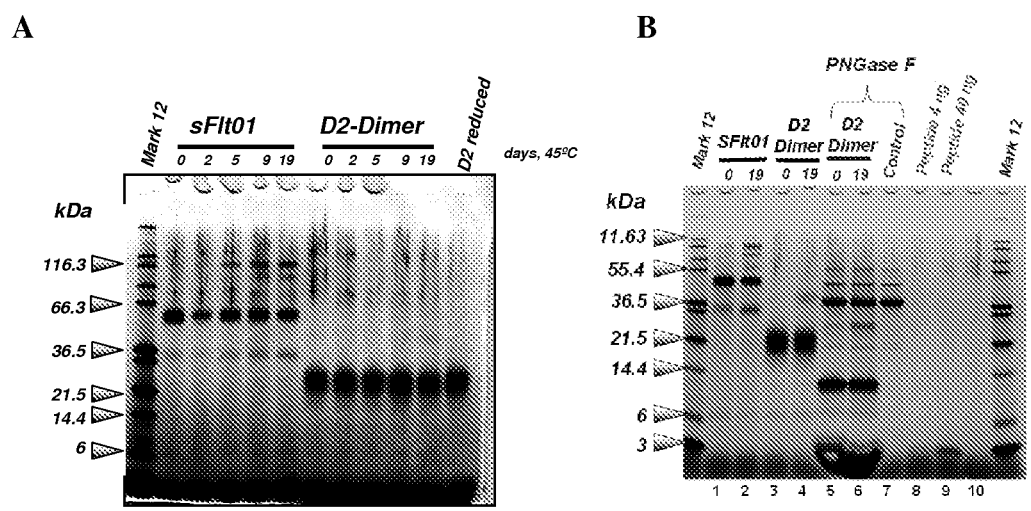
FIG. 8: Silver-stained reducing SDS PAGE (4-12% Bis-Tris/MES) of 50 ng protein is shown (with in silico intensification) in FIG. 8*a*. The sFLT01 control showed increasing amounts of a ~35 kDa product as well as a high MW aggregate of ~115 kDa. In contrast, the D2 dimer showed only the accumulation of a very weakly-staining diffuse product of ~40 kDa MW, which was more clearly visible when the 19-day incubation product (200 ng) was rerun on a reducing 12% Bis-Tris gel (FIG. 8*b*).

A stability study was undertaken to assess the susceptibility of the dimer to fragmentation at 45° C. as a surrogate for the stress of formulation, since the MW fragmentation pattern seen after extended incubations at elevated temperature is indistinguishable from that obtained after formulation and subsequent release from a variety of matrices. Dimer (0.25 mg/ml) was incubated in PBS with 1× HALT protease inhibitor cocktail with EDTA (Pierce) at 45° C. and aliquots drawn and flash frozen at −80° C. Unmodified sFLT01 at the same concentration was used as a control. Silver-stained reducing SDS PAGE (4-12% Bis-Tris/MES) of 50 ng protein is shown (with in silico intensification) in FIG. 8a. The sFLT01 control showed increasing amounts of a ~35 kDa product as well as a high MW aggregate of ~115 kDa. In contrast, the D2 dimer showed only the accumulation of a very weakly-staining diffuse product of ~40 kDa MW, which was more clearly visible when the 19-day incubation product (200 ng) was rerun on a reducing 12% Bis-Tris gel (FIG. 8b). PNGase F treatment (lanes 5,6) showed a major band migrating at the expected MW of the deglycosylated D2 polypeptide (12.3 kDa) and the presence of a higher MW product (~25 kDa) consistent with the diffuse band seen without PNGase F treatment. Cleavage of D2 at the same site as in sFLT01 would be expected to lead to a 21aa 2.5 kDa peptide. A similar MW peptide (MOG35-55, 2.6 kDa, lanes 8,9) was detectable at 4 ng, equivalent to the amount of peptide fragment expected from 10% cleavage of D2. No similar peptide was observed in the incubation mixture. These results show that the D2 dimer are more stable than sFLT01 to formulation stress.

Figure 10:
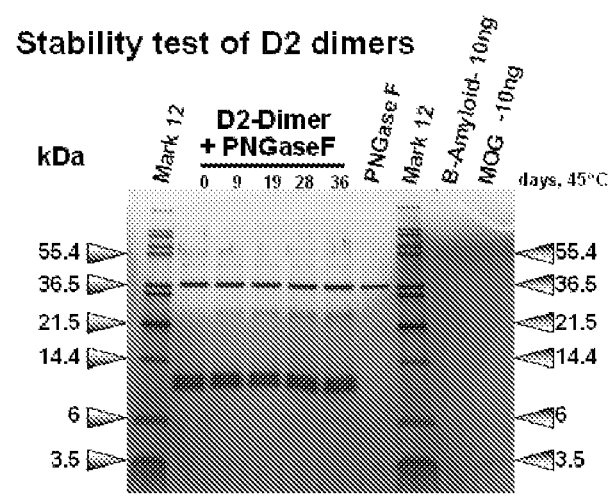
FIG. 10 shows stability test of D2 dimers.

D2 dimers prepared by copper oxidation were shown to be stable for 19 days at 45° C. using reducing SDS PAGE stained with silver. Although the patterns were very similar over time, as seen previously D2 monomer ran as a broad band of ~24 kDa, substantially above the polypeptide MW of 12.3 kDa probably due to heterogeneous glycosylation. The MW of the D2-Cys by MALDI was found to be 16.6 kDa. The breadth of the band may have obscured a small decrease in MW by fragmentation and the gel may have had limited sensitivity for detecting the low MW peptide fragments expected from cleavage at the same site as occurs in sFLT01. PNGase F was used to deglycosylate the samples prior to gel electrophoresis. Samples from the same stability study extended to 36 days were then analyzed by SDS PAGE after PNGase F treatment in the presence of reducing agent. A SDS PAGE gel stained with silver is shown in FIG. 10. D2 migrated as a doublet at approximately the expected MW (12 kDa) which did not change during the course of incubation. Only weakly-detectable amounts of material at slightly lower MW than the D2 doublet was observed, as well as a small amount of aggregate migrating at the MW expected for a non-reduced dimer. No peptides of the MW expected for cleavage at the principal sFLT01 site (2.5 kDa) were seen. (PNGase F appeared as a single band at ~37 kDa).

Figure 11:
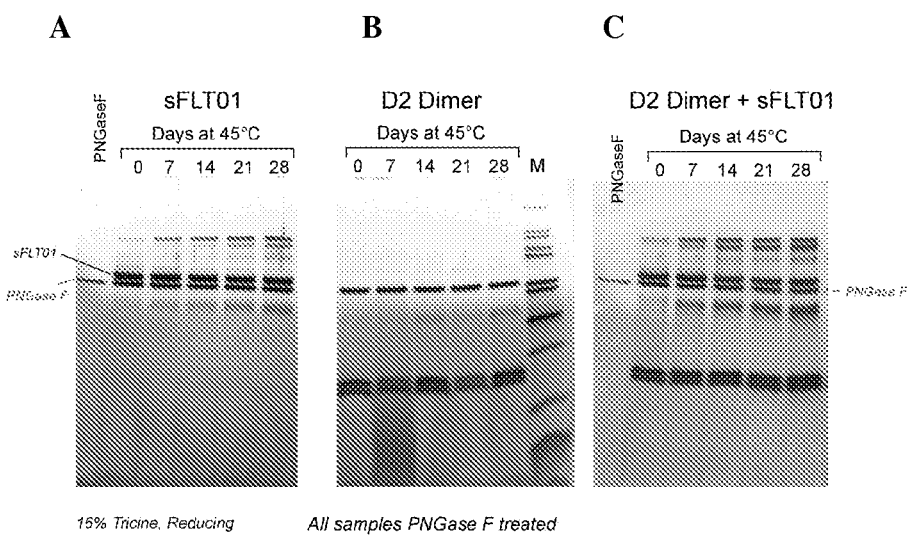

To determine if subtle differences in the reaction conditions for the sFLT01 or D2 dimer in the stability study in FIG. 10, a second study was performed. Proteins (0.25 mg/ml) were incubated either separately or as a co-mixture in PBS+protease inhibitors as described above, aliquots drawn and frozen at −80 C. After 28 days, samples were thawed and deglycosylated exhaustively with PNGase F and analyzed by reducing SDS PAGE followed by silver staining (FIG. 11). This showed production of the expected degradation product of sFLT01 (left), and accumulation of a slight amount of aggregate with the D2 dimer (center). When incubated together, D2 dimer again showed little or no fragmentation. However, the sFLT01 fragmentation product (migrating below the PNGase F) was clearly visible after 7 days and increased in abundance with longer incubation.

Figure 12:
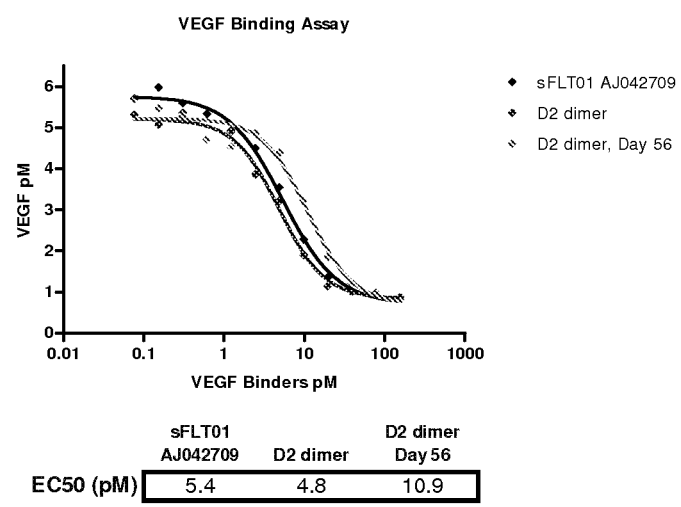
Figure 13:
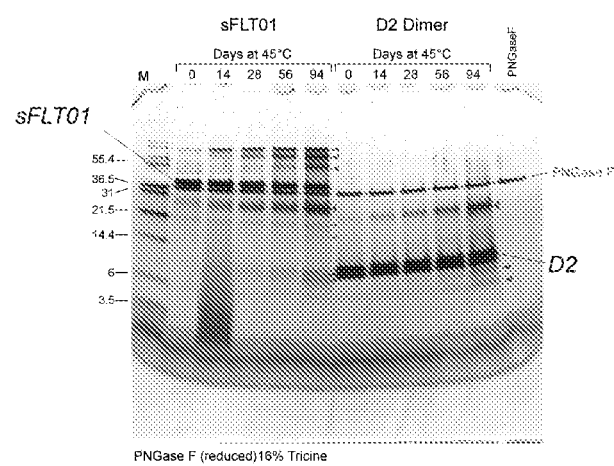
Figure 14:
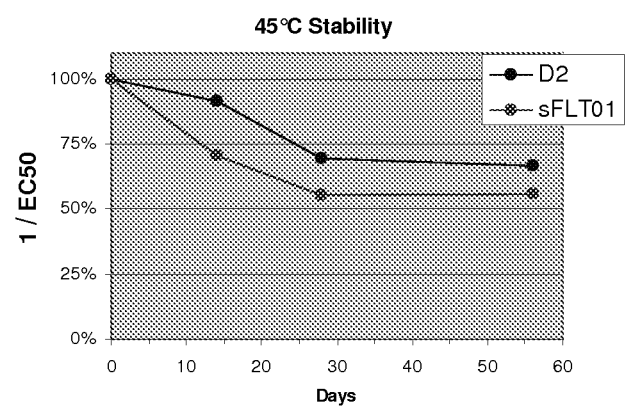
Figure 15:
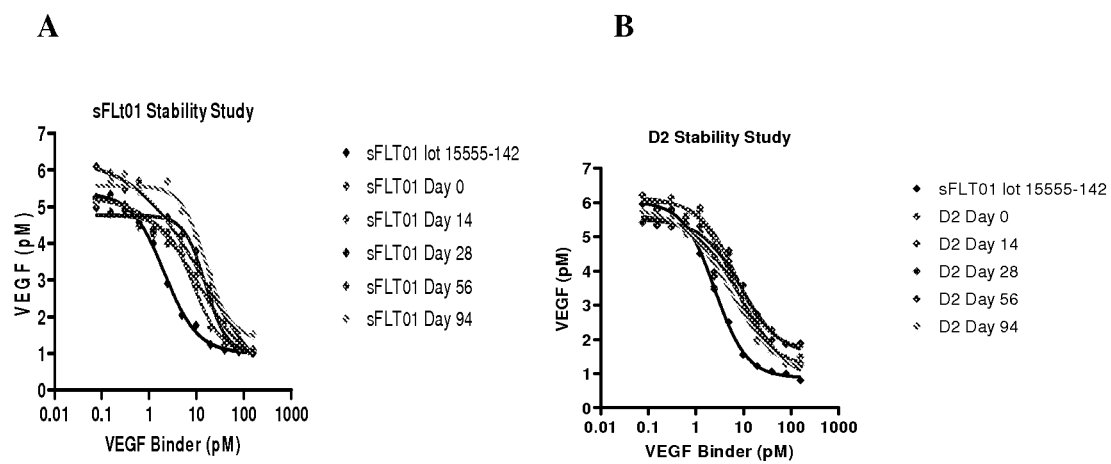

The activity of the D2 dimer after extended incubation was determined by VEGF ELISA. A fresh preparation of dimer was assayed against dimer incubated at 45° C. for 56 days. The results (FIG. 12) show that the dimer retained at least 50% activity after 56 days. An elevated temperature (45° C.) stability study was initiated to assess whether the D2 dimer would continue to show a greater resistance to fragmentation than sFLT01, as was concluded from initial studies. Fragmentation of sFLT01 at elevated temperature has been used as a surrogate for the stress of formulation into slow release particles since the patterns of fragmentation are nearly identical. Reactions were set up with 0.25 mg/ml protein in PBS with 1× protease inhibitors (Pierce) and samples taken at intervals and snap frozen at −80 C. After 94 days, the samples were thawed and an aliquot (0.5 ug) treated with 20 ng PNGase F overnight in the presence of βME and the products (0.2 ug) run on 16% Tricine-SDS PAGE and stained with silver. This showed accumulation of ~30 kDa and ~10 kDa cleavage products and three higher MW aggregates in the sFLT01 preparation, while D2 showed a small amount of ~10 kDa cleavage product and a modest amount of a higher MW aggregate band running near the mobility expected for unreduced dimer (FIG. 13). The activity of the products was then assessed by competitive VEGF ELISA (plots in FIG. 15). The initial activity of the sFLT01 in the reaction mixture was ~2-fold lower than expected, based on the sFLT01 control. The effect of the incubation on the activity (1/EC50) relative to time zero is plotted in FIG. 14. After 14 days, there was a significant difference in activity between D2 dimer and sFLT01, sFLT01 having lost ~30% activity while the D2 dimer <10%. After 28 days, the rate of decline slowed for both sFLT01 and D2, producing similar overall activity for both after 56 days. After 94 days, the D2 activity appeared to increase, likely due to evaporative concentration of the sample. Nevertheless, the data up to 56 days indicates the D2 dimer has higher thermal stability than sFLT01 and thus is likely to show greater resistance to the stress of formulation into slow-release depots.

Example 4

Oligomerized VEGF Antagonist for Treating Osteoarthritis

Animal models of osteoarthritis can be administered with various doses of VEGF antagonist oligomer composition of the invention at various time intervals Animal models of osteoarthritis are well known in the art. For example, these animal models are described in Stevenson et al., 2006, In Vivo Models of Inflammation, 2nd Ed., Vol. I, pages 65-82, *Birkhauser Basel Publication*. Administration methods are also well known in the art. For example, methods of administration in mice and rat are described in WO 2006/031689 and Matsumoto et al., 2009, *Arthritis & Rheumatism*, vol. 60, pages 1390-1405.

VEGF may contribute to osteoarthritis pain and cartilage and bone structural changes by: 1) enhancing synovial inflammation, effusion, and angiogenesis, 2) promoting blood vessel invasion into cartilage, 3) contributing to bone marrow edema, 4) promoting local re-initiation of endochondral bone formation, resulting in tidemark duplication, bone sclerosis, chondrocyte hypertrophy, and cartilage thinning. Therefore, blocking VEGF signaling is of benefit to relieve osteoarthritis pain and/or to protect joint structure.

In animal models, blocking VEGF by administering VEGF antagonist oligomer composition of the invention may result in decreased synovial inflammation and hyperplasia, two factors correlated with osteoarthritis pain in humans. Traits associated with osteoarthritis pain and cartilage and bone structural changes can be measured in treated as well as control animals. Half lives of VEGF antagonist oligomer composition of the invention can also be measured.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A vascular endothelial growth factor (VEGF) antagonist oligomer comprising: a plurality of monomers operably linked to each other, wherein each monomer comprises the second VEGF binding domain (D2) of FMS-like tyrosine kinase-1 (FLT-1), and wherein the plurality of monomers are linked to each other through a non-protein polymer.

2. The oligomer of claim 1, wherein the oligomer enhances the affinity for binding VEGF relative to FLT-1.

3. The oligomer of claim 1, wherein the oligomer antagonizes the binding of VEGF to FLT-1.

4. The oligomer of claim 1, wherein the plurality of monomers are linked to each other through a multifunctional PEG.

5. The oligomer of claim 4, wherein the plurality of monomers are linked to each other through bis-maleimide PEGs.

6. The oligomer of claim 1, wherein the oligomer is a dimer.

7. The oligomer of claim 1, wherein the oligomer is a trimer.

8. The oligomer of claim 1, wherein the oligomer is a tetramer.

9. The oligomer of claim 1, wherein the second VEGF binding domain (D2) comprises a C-terminal cysteine.

10. The oligomer of claim 1, wherein each monomer comprises the amino acid sequence set forth in SEQ ID NO:1.

11. The oligomer of claim 10, wherein said amino acid sequence is encoded by the nucleic acid sequence set forth in SEQ ID NO: 2.

12. A pharmaceutical composition comprising: a therapeutically effective amount of the oligomer of claim 1 and a pharmaceutically acceptable carrier.

13. A method for treating a disease or disorder associated with the binding of VEGF to its receptor, in a subject, wherein the disease or disorder is pathologic angiogenesis and/or a vascular permeability disorder, the method comprising: administering to said subject a therapeutically effective amount of the oligomer of claim 1.

14. The method of claim 13, wherein said disease causes chronic pain.

15. The method of claim 13, wherein said disease is a pathologic angiogenesis.

16. The method of claim 13, wherein said disorder is a vascular permeability disorder.

17. A method for blocking VEGF signaling in a subject, the method comprising: administering to said subject a therapeutically effective amount of the oligomer of claim 1.

18. A method for treating a disease or disorder associated with the binding of VEGF to its receptor, in a subject, wherein the disease or disorder is pathologic angiogenesis and/or a vascular permeability disorder, the method comprising: administering to said subject a therapeutically effective amount of a vascular endothelial growth factor (VEGF) antagonist oligomer, said oligomer comprising a plurality of monomers operably linked to each other, wherein each monomer comprises the second VEGF binding domain (D2) of FMS-like tyrosine kinase-1 (FLT-1).

19. The method of claim 18, wherein the oligomer enhances the affinity for binding VEGF relative to FLT-1.

20. The method of claim 18, wherein the oligomer antagonizes the binding of VEGF to FLT-1.

21. The method of claim 18, wherein the plurality of monomers are linked to each other through a simple covalent bond, a flexible peptide linker, or a disulfide bridge.

22. The method of claim 18, wherein at least one of the plurality of monomers is PEGylated.

23. The method of claim 18, wherein the oligomer is a dimer.

24. The method of claim 18, wherein the oligomer is a trimer.

25. The method of claim 18, wherein the oligomer is a tetramer.

26. The method of claim 18, wherein the second VEGF binding domain (D2) comprises a C-terminal cysteine.

27. The method of claim 18, wherein each monomer comprises the amino acid sequence set forth in SEQ ID NO:1.

28. The method of claim 27, wherein said amino acid sequence is encoded by the nucleic acid sequence set forth in SEQ ID NO: 2.

29. The method of claim 18, wherein said disease causes chronic pain.

30. The method of claim 18, wherein said disease is a pathologic angiogenesis.

31. The method of claim 18, wherein said disorder is a vascular permeability disorder.

32. A method for blocking VEGF signaling in a subject, the method comprising: administering to said subject a therapeutically effective amount of a vascular endothelial growth factor (VEGF) antagonist oligomer, said oligomer comprising a plurality of monomers operably linked to each other, wherein each monomer comprises the second VEGF binding domain (D2) of FMS-like tyrosine kinase-1 (FLT-1).

* * * * *

SEQUENCE LISTING

```
<160> NUMBER OF SEQ ID NOS: 4

<210> SEQ ID NO 1
<211> LENGTH: 94
<212> TYPE: PRT
<213> ORGANISM: Homo sapiens

<400> SEQUENCE: 1

Arg Pro Phe Val Glu Met Tyr Ser Glu Ile Pro Glu Ile Ile His Met
1               5                   10                  15

Thr Glu Gly Arg Glu Leu Val Ile Pro Cys Arg Val Thr Ser Pro Asn
            20                  25                  30

Ile Thr Val Thr Leu Lys Lys Phe Pro Leu Asp Thr Leu Ile Pro Asp
        35                  40                  45

Gly Lys Arg Ile Ile Trp Asp Ser Arg Lys Gly Phe Ile Ile Ser Asn
    50                  55                  60

Ala Thr Tyr Lys Glu Ile Gly Leu Leu Thr Cys Glu Ala Thr Val Asn
65                  70                  75                  80

Gly His Leu Tyr Lys Thr Asn Tyr Leu Thr His Arg Gln Thr
                85                  90

<210> SEQ ID NO 2
<211> LENGTH: 282
<212> TYPE: DNA
<213> ORGANISM: Homo sapiens

<400> SEQUENCE: 2
agacctttcg tagagatgta cagtgaaatc cccgaaatta tacacatgac tgaaggaagg      60
gagctcgtca ttccctgccg ggttacgtca cctaacatca ctgttacttt aaaaaagttt     120
ccacttgaca ctttgatccc tgatggaaaa cgcataatct gggacagtag aaagggcttc     180
```

```
atcatatcaa atgcaacgta caaagaaata gggcttctga cctgtgaagc aacagtcaat        240
gggcatttgt ataagacaaa ctatctcaca catcgacaaa cc                          282

<210> SEQ ID NO 3
<211> LENGTH: 131
<212> TYPE: PRT
<213> ORGANISM: Homo sapiens

<400> SEQUENCE: 3

Met Val Ser Tyr Trp Asp Thr Gly Val Leu Leu Cys Ala Leu Leu Ser
1               5                   10                  15

Cys Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
    50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Glu Asp Gln Val Asp Pro Arg Leu Ile Asp
        115                 120                 125

Gly Lys Cys
    130

<210> SEQ ID NO 4
<211> LENGTH: 402
<212> TYPE: DNA
<213> ORGANISM: Homo sapiens

<400> SEQUENCE: 4
gccaccatgg tcagctactg ggacaccggg gtcctgctgt gcgcgctgct cagctgtctg        60
cttctcacag gatctggtag acctttcgta gagatgtaca gtgaaatccc cgaaattata       120
cacatgactg aaggaaggga gctcgtcatt ccctgccggg ttacgtcacc taacatcact       180
gttactttaa aaaagtttcc acttgacact ttgatccctg atggaaaacg cataatctgg       240
gacagtagaa agggcttcat catatcaaat gcaacgtaca agaaataggg cttctgacc        300 tgtgaagcaa cagtcaatgg gcatttgtat aagacaaact atctcacaca tcgacaaacc      360
gaagatcaag tggatccacg cctcatcgat ggcaaatgct ga                          402
```